(12) United States Patent
Pietropaolo et al.

(10) Patent No.: US 6,930,181 B1
(45) Date of Patent: Aug. 16, 2005

(54) ANTIGEN ASSOCIATED WITH TYPE 1 DIABETES MELLITUS

(75) Inventors: Massimo Pietropaolo, Brookline, MA (US); George S. Eisenbarth, Wellesley, MA (US)

(73) Assignee: Joslin Diabetes Center, Inc., Boston, MA (US)

(*) Notice: Subject to any disclaimer, the term of this patent is extended or adjusted under 35 U.S.C. 154(b) by 0 days.

(21) Appl. No.: 08/467,605

(22) Filed: Jun. 6, 1995

Related U.S. Application Data

(60) Division of application No. 08/307,485, filed on Sep. 16, 1994, now Pat. No. 5,891,437, which is a continuation of application No. 07/901,523, filed on Jun. 19, 1992, now abandoned, which is a continuation-in-part of application No. 07/788,118, filed on Nov. 1, 1991, now abandoned.

(51) Int. Cl.$^7$ .............................................. C07H 21/04
(52) U.S. Cl. ....................... 536/23.5; 536/23.1; 514/44; 424/185.1
(58) Field of Search ............................ 435/69.3, 172.3; 536/23.2, 23.5, 23.1; 424/152.1, 185.1; 514/44

(56) References Cited

U.S. PATENT DOCUMENTS

| | | | |
|---|---|---|---|
| 4,612,365 A | 9/1986 | Birr et al. | 530/301 |
| 4,681,760 A | 7/1987 | Fathman | 424/85 |
| 4,761,371 A | 8/1988 | Bell et al. | 435/68 |
| 4,904,481 A | 2/1990 | Fathman | 424/85.8 |
| 5,114,844 A | 5/1992 | Cohen et al. | 435/7.21 |

FOREIGN PATENT DOCUMENTS

EP   0 192 392   2/1986

OTHER PUBLICATIONS

Erlander et al. (1991) "Two Genes Encode Distinct Glutamate Decarboxylases" *Neuron* 7:91–100.
Hirayama et al. (1990) "Rapid Confirmation and Revision of the Primary Structure of Bovine Serum Albumin by Esims and Frit–Fab LC/MS" *Biochemical and Biophysical Research Communications* 173(2):639–646.
Houssaint et al. "Monoclonal Autoantibodies From Insulin–Dependent Diabetic Patients: Autoantibodies β–Cell Surface or Cytoplasmic Antigens" *Clinical Experimental Immunology* 82:44–51.
Hunkapiller et al. (1983) "Isolation of Microgram Quantities of Proteins From Polyacrylamide Gels for Amino Acid Sequence Analysis" *Methods in Emzymology* 91: 227–237.
*Immunology*, Roitt et al., Eds. (1989) (New York: Harper & Row) G1–G3 (Glossary).
Jaye et al. (1983) "Isolation of a human anti–haemophilic factor IX cDNA clone using a unique 52–Base Synthetic Oligonucleotide probe deduced from the amino acid sequence of bovin factor IX" *Nuc. Acid. Res.* 11(8):2325–2335.

Laver et al. (1990) "Epitopes on Protein Antigens: Misconceptions and Realities" *Cell* 61(4):553–556.
Martin et al. (1991) "Milk Proteins in the Etiology of Insulin–Dependent Diabetes Mellitus (IDDM)" *Annals of Medicine* 23:447–452.
Michelsen et al . (1991) "Cloning, Characterization, and Autoimmune Recognition of Rat Islet Glutamic Acid Decarboxylase In Insulin–Dependent Diabetes Mellitus" *PNAS USA* 88:8754–8758.
Morein (1990) "The Iscom: An Immunostimulating System" *Immunol. Letters* 25:281–284.
Palmer et al. (1983) "Insulin Antibodies in Insulin–Dependent Diabetics Before Insulin Treatment" *Science* 222:1337–1339.
Petrov et al. (1990) "Modelling of type 1 diabetes with monoclonal antibody ICA–1" *Biomedical Science* 1:144–150.
Petrov et al. (1990) "Approaches to Immunodiagnostics IDDM Based on p64–69 Beta–Cell Antigen Family and Corresponding Monoclonal Antibody ICA–1" *Proceedings of the Immunology of Diabetes 10th International Workshop* (Jerusalem, Israel: Mar. 18–24) 9.
Pietropaolo et al. (1993) "Islet Cell Autoantigen 69 kD (ICA69) Molecular Cloning and Characterization of a Novel Diabetes–associated Autoantigen" *J. Clin. Invest.* 92(1):359–371.
Pietropaolo et al. (1992) "Molecular Cloning and Characterization of a Novel Neuroendocrine Autoantigen (PM–1) Related to Type 1 Diabetes" *Diabetes* 41(Supp. 1):98A (Abstract # 356).
Pietropaolo et al. (1991) "Utilization of a human Agtil islet library to identify novel autoantigens associated with Type 1 Diabetes " *Diabetes* 40:1A (Abstract #2).
Srikanta et al. (1986) "Islet Cell Antigens Initial Studies of Their Biology and Function" *Molecular Biol. and Med.* 3:113–127.
Srikanta et al. (1986) "Islet Cell Proteins Defined by Monoclonal Islet Cell Antibody HISL–19" *Diabetes* 35:300–305.
Tanguay et al. (1990) "A Cytotoxic Monoclonal Autoantibody From the BB Rat Which Binds An Islet Cell Surface Protein" *Diabetes Research and Clinical Practice* 8:23–28.
Baekkeskov et al. (1990) "Identification of the 64K Autoantigen in Insulin–Dependent Diabetes as the GABA–synthesizing Enzyme Glutamic Acid Decarboxylase" *Nature* 347:151–156.
Dotta et al. (1988) "A Novel Neuroendocrine Cell Surface Glycoprotein: Identification, Isolation, and Initial Characterization" *Endocrinology* 122(4):1263–1268.
Eisenbarth (1986) "Type 1 Diabetes Mellitus" *New Eng. J. Medicine* 314:1360–1368.

*Primary Examiner*—Laurie A. Scheiner
(74) *Attorney, Agent, or Firm*—Fish & Richardson P.C.

(57) ABSTRACT

A 69 kD protein, designated PM-1, is expressed in human pancreatic islet cells and a human insulinoma. The amino acid sequence of the protein has been determined. Autoantibodies to the PM-1 protein have been found in sera of prediabetic patients. Natural, synthetic or recombinant forms of the PM-1 protein can be used in immunochemical assays to detect anti-PM-1-autoantibodies and to identify patients at risk of developing diabetes.

20 Claims, 9 Drawing Sheets

```
CGGGCGGGGATACCCCAGGAGAGATGGGGGTCGAGGAGAGACCCCGGGAGTAGAGAGAGAAACTCACTC    71
CCCGAGTCCCCGACCCTCCCCAAGCAGTTATAATATAAACTTATCCTCTCATGCTTTTCCTGCCCCTT   142
CTCCCCAAATCATCAACAATAGAAGAAGAAACATG TCA GAC CAC AAA TGC AGT TAT CCC   205
                                    Met Ser Gly His Lys Cys Ser Tyr Pro    9
```

| TGG | GAC | TTA | CAG | GAT | CGA | TAT | GCT | CAA | GAT | AAG | TCA | GTT | AAT | AAG | ATG | CAA | 259 |
|---|---|---|---|---|---|---|---|---|---|---|---|---|---|---|---|---|---|
| Trp | Asp | Leu | Gln | Asp | Arg | Tyr | Ala | Gln | Asp | Lys | Ser | Val | Asn | Lys | Met | Gln | 27 |
|  |  |  |  |  |  |  |  |  |  |  |  |  | AMD |  |  |  |  |

| CAG | AGA | TAT | TGG | GAG | ACG | AAG | CAG | GCC | TTT | ATT | AAA | GCC | ACA | GGG | AAG | GAA | 313 |
|---|---|---|---|---|---|---|---|---|---|---|---|---|---|---|---|---|---|
| Gln | Arg | Tyr | Trp | Glu | Thr | Lys | Gln | Ala | Phe | Ile | Lys | Ala | Thr | Gly | Lys | Glu | 45 |

| GAT | GAA | CAT | GTT | GTT | GCC | TCT | GAC | GCG | GAT | GCC | AAG | CTA | GAG | CTG | TTT | 367 |
|---|---|---|---|---|---|---|---|---|---|---|---|---|---|---|---|---|
| Asp | Glu | His | Val | Val | Ala | Ser | Asp | Ala | Asp | Ala | Lys | Leu | Glu | Leu | Phe | 63 |

| CAT | TCA | ATT | CAG | AGA | ACC | TGT | CTG | GAC | TTA | TCG | AAA | GCA | ATT | GTA | CTC | TAT | CAA | 421 |
|---|---|---|---|---|---|---|---|---|---|---|---|---|---|---|---|---|---|---|
| His | Ser | Ile | Gln | Arg | Thr | Cys | Leu | Asp | Leu | Ser | Lys | Ala | Ile | Val | Leu | Tyr | Gln | 81 |
|  |  |  |  |  | CK2 |  |  |  |  |  |  |  |  |  |  |  |  |  |

| AAG | AGG | ATA | TGT | TTC | TCT | CAA | GAA | AAC | CTG | GGA | AAA | TTT | CTT | CGA | 475 |
|---|---|---|---|---|---|---|---|---|---|---|---|---|---|---|---|
| Lys | Arg | Ile | Cys | Phe | Ser | Gln | Glu | Asn | Leu | Gly | Lys | Phe | Leu | Arg | 99 |

| TCC | CAA | GGT | TTC | CAA | GAT | AAA | ACC | AGA | GCA | GGA | AAG | ATG | CAA | GCG | ACA | GGA | 529 |
|---|---|---|---|---|---|---|---|---|---|---|---|---|---|---|---|---|---|
| Ser | Gln | Gly | Phe | Gln | Asp | Lys | Thr | Arg | Ala | Gly | Lys | Met | Gln | Ala | Thr | Gly | 117 |

| AAG | GCC | CTC | TGC | TTT | TCT | CCC | CAG | AGG | TTG | GCC | TTA | CGA | AAT | CCT | TTG | TGT | 583 |
|---|---|---|---|---|---|---|---|---|---|---|---|---|---|---|---|---|---|
| Lys | Ala | Leu | Cys | Phe | Ser | Pro | Gln | Arg | Leu | Ala | Leu | Arg | Asn | Pro | Leu | Cys | 135 |

| CGA | TTT | CAC | CAA | GAA | GTG | GAG | ACT | TTT | CGG | CAT | CGG | GCC | ATC | TCA | GAT | ACT | TGG | 637 |
|---|---|---|---|---|---|---|---|---|---|---|---|---|---|---|---|---|---|---|
| Arg | Phe | His | Gln | Glu | Val | Glu | Thr | Phe | Arg | His | Arg | Ala | Ile | Ser | Asp | Thr | Trp | 153 |

| CTG | ACG | GTG | AAC | CGC | ATG | GAA | CGC | AGG | TGC | AGG | ACG | TAT | AGA | GGA | GCA | CTA | TTA | 691 |
|---|---|---|---|---|---|---|---|---|---|---|---|---|---|---|---|---|---|---|
| Leu | Thr | Val | Asn | Arg | Met | Glu | Arg | Arg | Cys | Arg | Thr | Tyr | Arg | Gly | Ala | Leu | leu | 171 |

FIG. 2A

```
TGG ATG AAG GAC GTG TCT CAG GAG CTT GAT CCA GAC CTC TAC AAG CAA ATG GAG   745
Trp Met Lys Asp Val Ser Gln Glu Leu Asp Pro Asp Leu Tyr Lys Gln Met Glu   189

AAG TTC AGG AAG GTG CAA ACA GTG CTT CGC GTG GCA CTT AAA AAC TTT GAC AAA   799
Lys Phe Arg Lys Val Gln Thr Val Leu Arg Val Ala Leu Lys Asn Phe Asp Lys   207

TTG AAG ATG GAT GTG TGT CAA AAA GTG GAT CTT CTT GGA GCG AGC AGA TGC AAT   853
Leu Lys Met Asp Val Cys Gln Lys Val Asp Leu Leu Gly Ala Ser Arg Cys Asn   225

CTC TTG TCT CAC ATG CTA GCA ACA TAC CAG ACT CTG CAT TTT TGG GAG           907
Leu Leu Ser His Met Leu Ala Thr Tyr Gln Thr Leu His Phe Trp Glu           243
                                        PKC

AAA ACT TCT CAC ACT ATG GCA GCC ATC ATG GAG AGT TTC AAA GGT TAT CAA CCA   961
Lys Thr Ser His Thr Met Ala Ala Ile His Glu Ser Phe Lys Gly Tyr Gln Pro   261
                                CK2

TAT GAA TTT ACT ACT TTA AAG AGC TTA CAA GAC CCT ATG AAA TTA GTT GAG      1015
Tyr Glu Phe Thr Thr Leu Lys Ser Leu Gln Asp Pro Met Lys Leu Val Glu       279

AAA GAG GAG AAG AAG AAA ATC CAG CAG GAA AGT ACA GAT GCA GCC GTG CAG      1069
Lys Glu Glu Lys Lys Lys Ile Asn Gln Glu Ser Thr Asp Ala Ala Val Gln       297
                                                AMP

GAG CCG AGC CAA TTA ATT TCA TTA GAG GAA AAC CAG CGC AAG GAA TCC TCT      1123
Glu Pro Ser Gln Leu Ile Ser Leu Glu Glu Asn Gln Arg Lys Glu Ser Ser       315
PKC                     CK2

AGT TTT AAG ACT GAA GAT GGA AAA AGT ATT TTA TCT GCC TTA GAC AAA GGC TCT  1177
Ser Phe Lys Thr Glu Asp Gly Lys Ser Ile Leu Ser Ala Leu Asp Lys Gly Ser   333

ACA CAT ACT GCA TGC TCA GGA CCC ATA GAT GAA CTA TTA GAC ATG AAA TCT GAG  1231
Thr His Thr Ala Cys Ser Gly Pro Ile Asp Glu Leu Leu Asp Met Lys Ser Glu   351
```

FIG. 2B

```
GAA GGT GCT TGC CTG GGA CCA GTG GCA GGG ACC CCG GAA CCT GAA GGT GCT GAC   1285
Glu Gly Ala Cys Leu Gly Pro Val Ala Gly Thr Pro Glu Pro Glu Gly Ala Asp    369
                                            *           CK2

AAA GAT GAC CTG CTG TTG AGT GAG ATC TTC AAT GCT TCC TTG GAA GAG            1339
Lys Asp Asp Leu Leu Leu Ser Glu Ile Phe Asn Ala Ser Leu Glu Glu            387

GGC GAG TTC AGC AAA GAG TGG GCC GCT GTG TTT GGA GAC GGC CAA GGC            1393
Gly Glu Phe Ser Lys Glu Trp Ala Ala Val Phe Gly Asp Gly Gln Gly            405

CCA GTG CCC ACT ATG GCC CTG GGA GAG CCA GAC CCC AAG GCC CAG ACA GGC TCA    1447
Pro Val Pro Thr Met Ala Leu Gly Glu Pro Asp Pro Lys Ala Gln Thr Gly Ser     423

GGT TTC CTT CCT TCG CAG CTT TTA GAC CAA AAT ATG AAA GAC TTA CAG GCC TCG    1501
Gly Phe Leu Pro Ser Gln Leu Leu Asp Gln Asn Met Lys Asp Leu Gln Ala Ser     441
                                                                    CK2

CTA CAA GAA CCT GCT AAG GCT GCC TCA GAC CTG ACT GCC TGG TTC AGC CTC TTC    1555
Leu Gln Glu Pro Ala Lys Ala Ala Ser Asp Leu Thr Ala Trp Phe Ser Leu Phe     459
                                                        CK2

GCT GAC CTC GAC CCA CTC TCA AAT CCT GAT GCT GTT GGG AAA ACC GAT AAA GAA    1609
Ala Asp Leu Asp Pro Leu Ser Asn Pro Asp Ala Val Gly Lys Thr Asp Lys Glu     477

CAC GAA TTG CTC AAT GCA TGAATCTGTACCCTTCGGAGGGCACTCACATGCCGCCCCCAGCAGCT    1674
His Glu Leu Leu Asn Ala END                                                 483

CCCCTGGGGGCTAGCAGAAGTATAAAGTGATCAGTATGCTGTTTAATAATTATGTGCCATTTTAATAAAA     1745
TGAAAGGGTCAACGGCCCCTGTTAAAAAAAAAAAAAAA                                    1785
```

V |F D K L K| H L |V| D    BSA   373

S |E| E |G A C L| G |P| V   PM-1  351
  |*|

E |D| K |G A C L| L |P| K   BSA   172

FIG. 4

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1785 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 179..1628

(xi) SEQUENCE DESCRIPTION: SEQ ID NO:1:

```
CGGGCGGGGG ATACCCCAGG AGATGGGGGT CGAGGAGAGA CCCCGGGGAG TAGAGAGAGA      60

GAAACTCACT CCCCGAGTCC CCGACCCTCC CCAAGCAAGG TTATAATATA ACTTATCCTC     120

TCATGCTTTT TTCCTGCCCC TTCTCCCCAA ATCATCAACA ATAGAAGAAG AAGAAAAC      178

ATG TCA GGA CAC AAA TGC AGT TAT CCC TGG GAC TTA CAG GAT CGA TAT      226
Met Ser Gly His Lys Cys Ser Tyr Pro Trp Asp Leu Gln Asp Arg Tyr
 1               5                  10                  15

GCT CAA GAT AAG TCA GTT GTA AAT AAG ATG CAA CAG AGA TAT TGG GAG      274
Ala Gln Asp Lys Ser Val Val Asn Lys Met Gln Gln Arg Tyr Trp Glu
             20                  25                  30

ACG AAG CAG GCC TTT ATT AAA GCC ACA GGG AAG AAG GAA GAT GAA CAT      322
Thr Lys Gln Ala Phe Ile Lys Ala Thr Gly Lys Lys Glu Asp Glu His
         35                  40                  45

GTT GTT GCC TCT GAC GCG GAC CTG GAT GCC AAG CTA GAG CTG TTT CAT      370
Val Val Ala Ser Asp Ala Asp Leu Asp Ala Lys Leu Glu Leu Phe His
     50                  55                  60
```

-continued

```
TCA ATT CAG AGA ACC TGT CTG GAC TTA TCG AAA GCA ATT GTA CTC TAT      418
Ser Ile Gln Arg Thr Cys Leu Asp Leu Ser Lys Ala Ile Val Leu Tyr
 65                  70                  75                  80

CAA CAG AGG ATA TGT TTC TTG TCT CAA GAA GAA AAC GAA CTG GGA AAA      466
Gln Gln Arg Ile Cys Phe Leu Ser Gln Glu Glu Asn Glu Leu Gly Lys
                     85                  90                  95

TTT CTT CGA TCC CAA GGT TTC CAA GAT AAA ACC AGA GCA GGA AAG ATG      514
Phe Leu Arg Ser Gln Gly Phe Gln Asp Lys Thr Arg Ala Gly Lys Met
                100                 105                 110

ATG CAA GCG ACA GGA AAG GCC CTC TGC TTT TCT TCC CAG CAA AGG TTG      562
Met Gln Ala Thr Gly Lys Ala Leu Cys Phe Ser Ser Gln Gln Arg Leu
            115                 120                 125

GCC TTA CGA AAT CCT TTG TGT CGA TTT CAC CAA GAA GTG GAG ACT TTT      610
Ala Leu Arg Asn Pro Leu Cys Arg Phe His Gln Glu Val Glu Thr Phe
        130                 135                 140

CGG CAT CGG GCC ATC TCA GAT ACT TGG CTG ACG GTG AAC CGC ATG GAA      658
Arg His Arg Ala Ile Ser Asp Thr Trp Leu Thr Val Asn Arg Met Glu
145                 150                 155                 160

CAG TGC AGG ACG GAA TAT AGA GGA GCA CTA TTA TGG ATG AAG GAC GTG      706
Gln Cys Arg Thr Glu Tyr Arg Gly Ala Leu Leu Trp Met Lys Asp Val
                165                 170                 175

TCT CAG GAG CTT GAT CCA GAC CTC TAC AAG CAA ATG GAG AAG TTC AGG      754
Ser Gln Glu Leu Asp Pro Asp Leu Tyr Lys Gln Met Glu Lys Phe Arg
                180                 185                 190

AAG GTG CAA ACA CAA GTG CGC CTT GCA AAA AAA AAC TTT GAC AAA TTG      802
Lys Val Gln Thr Gln Val Arg Leu Ala Lys Lys Asn Phe Asp Lys Leu
            195                 200                 205

AAG ATG GAT GTG TGT CAA AAA GTG GAT CTT CTT GGA GCG AGC AGA TGC      850
Lys Met Asp Val Cys Gln Lys Val Asp Leu Leu Gly Ala Ser Arg Cys
        210                 215                 220

AAT CTC TTG TCT CAC ATG CTA GCA ACA TAC CAG ACC ACT CTG CTT CAT      898
Asn Leu Leu Ser His Met Leu Ala Thr Tyr Gln Thr Thr Leu Leu His
225                 230                 235                 240

TTT TGG GAG AAA ACT TCT CAC ACT ATG GCA GCC ATC CAT GAG AGT TTC      946
Phe Trp Glu Lys Thr Ser His Thr Met Ala Ala Ile His Glu Ser Phe
                245                 250                 255

AAA GGT TAT CAA CCA TAT GAA TTT ACT ACT TTA AAG AGC TTA CAA GAC      994
Lys Gly Tyr Gln Pro Tyr Glu Phe Thr Thr Leu Lys Ser Leu Gln Asp
                260                 265                 270

CCT ATG AAA AAA TTA GTT GAG AAA GAA GAG AAG AAG AAA ATC AAC CAG     1042
Pro Met Lys Lys Leu Val Glu Lys Glu Glu Lys Lys Lys Ile Asn Gln
            275                 280                 285

CAG GAA AGT ACA GAT GCA GCC GTG CAG CAG CCG AGC CAA TTA ATT TCA     1090
Gln Glu Ser Thr Asp Ala Ala Val Gln Gln Pro Ser Gln Leu Ile Ser
        290                 295                 300

TTA GAG GAA GAA AAC CAG CGC AAG GAA TCC TCT AGT TTT AAG ACT GAA     1138
Leu Glu Glu Glu Asn Gln Arg Lys Glu Ser Ser Ser Phe Lys Thr Glu
305                 310                 315                 320

GAT GGA AAA AGT ATT TTA TCT GCC TTA GAC AAA GGC TCT ACA CAT ACT     1186
Asp Gly Lys Ser Ile Leu Ser Ala Leu Asp Lys Gly Ser Thr His Thr
                325                 330                 335

GCA TGC TCA GGA CCC ATA GAT GAA CTA TTA GAC ATG AAA TCT GAG GAA     1234
Ala Cys Ser Gly Pro Ile Asp Glu Leu Leu Asp Met Lys Ser Glu Glu
                340                 345                 350

GGT GCT TGC CTG GGA CCA GTG GCA GGG ACC CCG GAA CCT GAA GGT GCT     1282
Gly Ala Cys Leu Gly Pro Val Ala Gly Thr Pro Glu Pro Glu Gly Ala
            355                 360                 365

GAC AAA GAT GAC CTG CTG CTG TTG AGT GAG ATC TTC AAT GCT TCC TCC     1330
Asp Lys Asp Asp Leu Leu Leu Leu Ser Glu Ile Phe Asn Ala Ser Ser
```

-continued

```
            370              375              380
TTG GAA GAG GGC GAG TTC AGC AAA GAG TGG GCC GCT GTG TTT GGA GAC      1378
Leu Glu Glu Gly Glu Phe Ser Lys Glu Trp Ala Ala Val Phe Gly Asp
385                 390              395              400

GGC CAA GTG AAG GAG CCA GTG CCC ACT ATG GCC CTG GGA GAG CCA GAC      1426
Gly Gln Val Lys Glu Pro Val Pro Thr Met Ala Leu Gly Glu Pro Asp
                405              410              415

CCC AAG GCC CAG ACA GGC TCA GGT TTC CTT CCT TCG CAG CTT TTA GAC      1474
Pro Lys Ala Gln Thr Gly Ser Gly Phe Leu Pro Ser Gln Leu Leu Asp
            420              425              430

CAA AAT ATG AAA GAC TTA CAG GCC TCG CTA CAA GAA CCT GCT AAG GCT      1522
Gln Asn Met Lys Asp Leu Gln Ala Ser Leu Gln Glu Pro Ala Lys Ala
            435              440              445

GCC TCA GAC CTG ACT GCC TGG TTC AGC CTC TTC GCT GAC CTC GAC CCA      1570
Ala Ser Asp Leu Thr Ala Trp Phe Ser Leu Phe Ala Asp Leu Asp Pro
    450              455              460

CTC TCA AAT CCT GAT GCT GTT GGG AAA ACC GAT AAA GAA CAC GAA TTG      1618
Leu Ser Asn Pro Asp Ala Val Gly Lys Thr Asp Lys Glu His Glu Leu
465              470              475              480

CTC AAT GCA TGA ATCTGTAC CCTTCGGAGG GCACTCACAT GCCGCCCCA             1668
Leu Asn Ala *

GCAGCTCCCC TGGGGGCTAG CAGAAGTATA AAGTGATCAG TATGCTGTTT TAATAATTAT    1728

GTGCCATTTT AATAAAATGA AAGGGTCAAC GGCCCTGTTA AAAAAAAAAA AAAAAAA       1785

(2) INFORMATION FOR SEQ ID NO:2:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Arg Tyr Trp Glu
                20                  25                  30

Thr Lys Gln Ala Phe Ile Lys Ala Thr Gly Lys Lys Glu Asp Glu His
            35                  40                  45

Val Val Ala Ser Asp Ala Asp Leu Asp Ala Lys Leu Glu Leu Phe His
        50                  55                  60

Ser Ile Gln Arg Thr Cys Leu Asp Leu Ser Lys Ala Ile Val Leu Tyr
65                  70                  75                  80

Gln Gln Arg Ile Cys Phe Leu Ser Gln Glu Glu Asn Glu Leu Gly Lys
                85                  90                  95

Phe Leu Arg Ser Gln Gly Phe Gln Asp Lys Thr Arg Ala Gly Lys Met
            100                 105                 110

Met Gln Ala Thr Gly Lys Ala Leu Cys Phe Ser Ser Gln Gln Arg Leu
        115                 120                 125

Ala Leu Arg Asn Pro Leu Cys Arg Phe His Gln Glu Val Glu Thr Phe
    130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
```

-continued

```
                180                 185                 190
Lys Val Gln Thr Gln Val Arg Leu Ala Lys Lys Asn Phe Asp Lys Leu
            195                 200                 205

Lys Met Asp Val Cys Gln Lys Val Asp Leu Leu Gly Ala Ser Arg Cys
            210                 215                 220

Asn Leu Leu Ser His Met Leu Ala Thr Tyr Gln Thr Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
                260                 265                 270

Pro Met Lys Lys Leu Val Glu Lys Glu Glu Lys Lys Lys Ile Asn Gln
            275                 280                 285

Gln Glu Ser Thr Asp Ala Ala Val Gln Gln Pro Ser Gln Leu Ile Ser
            290                 295                 300

Leu Glu Glu Glu Asn Gln Arg Lys Glu Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
            355                 360                 365

Asp Lys Asp Asp Leu Leu Leu Ser Glu Ile Phe Asn Ala Ser Ser
            370                 375                 380

Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
                420                 425                 430

Gln Asn Met Lys Asp Leu Gln Ala Ser Leu Gln Glu Pro Ala Lys Ala
            435                 440                 445

Ala Ser Asp Leu Thr Ala Trp Phe Ser Leu Phe Ala Asp Leu Asp Pro
    450                 455                 460

Leu Ser Asn Pro Asp Ala Val Gly Lys Thr Asp Lys Glu His Glu Leu
465                 470                 475                 480

Leu Asn Ala
```

ANTIGEN ASSOCIATED WITH TYPE 1 DIABETES MELLITUS

RELATED APPLICATION

This application is a divisional application of Ser. No. 08/307,485 filed on Sep. 16, 1994, now U.S. Pat. No. 5,891,437, which in turn is a continuation application of Ser. No. 07/901,523 filed on Jun. 19, 1992, abandoned, which is a continuation-in-part application of Ser. No. 07/788,118 filed on Nov. 1, 1991, abandoned. The contents of all of the aforementioned application(s) are hereby incorporated by reference.

This application is a continuation-in-part of U.S. Ser. No. 788,118, filed Nov. 1, 1991, the contents of which are incorporated herein by reference.

GOVERNMENT SUPPORT

The work leading to this invention was supported, in part, by research grants from the United States government.

BACKGROUND OF THE INVENTION

There is evidence that insulin-dependent diabetes mellitus (IDDM) is a chronic autoimmune disease in which the presence of autoantibodies such as cytoplasmic islet cell antibodies (ICA), anti-glutamic acid decarboxylase (GAD) autoantibodies and anti-insulin autoantibodies are found years before the clinical onset of the disease (Eisenbarth, G. S. (1986) *N. Engl. J. Med.* 314:1360–1368). A common feature of Type I diabetes and other autoimmune diseases is a humoral immune response that can be manifested by the appearance of autoantibodies against cellular proteins (Tan, E. M. (1991) *Cell* :841–842). To date, only a few autoantigens associated with Type I diabetes mellitus have been identified, namely insulin (Palmer, J. P. et al (1983) *Science* 222:1337–1339), GAD (Baekkeskov, S. et al. (1990) *Nature* 347:151–156) and carboxypeptidase H (Castano, L. et al. (1991) *J. Clin. Endocr. Metab.* 73:1197–1201), and the glycolipids GT3 (Gillard, B. K., et al. (1989) *Journal Immunol. Methods* 142:3826–3832) and GM2-1 (Dotta, F., et al. (1992) *Endocrinology* 130:37–42).

Recently cDNA encoding a fragment of carboxypeptidase H, a granule-associated enzyme, has been reported to react with sera from prediabetic patients (Gillard, B. K., et al, supra) and another protein expressed in a λgtll phage from a human islet library appear to be recognized by IDDM sera (Rabin, D. U., et al. (1992) *Diabetes* 11:183–186). Cellular proteins of unknown sequence whose molecular weights are 38 kD (Roep, B. O., et al. (1991) *Lancet* 337:1439–1441), 52 kD (Karounos, D. G., and J. W. Thomas (1990) *Diabetes* 89:1085–1090), and 69 kD (Martin, J. M., et al. (1991) *Ann. Med,* 23:447–452), have also been reported to be recognized by a humoral and/or a cellular immune response. It is of interest that almost all patients with Type I diabetes have elevated levels of IgG anti-bovine serum albumin (BSA) antibodies which precipitate a $M_r$ 69,000 islet peptide which may represent a target antigen for cow milk induced islet autoimmunity (Martin, J. M., et al., supra; and Dosh, H-M, et al. (1991) *Pediatr. Adolesc. Endocrinol.* 21:). The identification of additional antigens associated with the development of diabetes could improve the ability of clinicians to evaluate the risk of development of the disease.

SUMMARY OF THE INVENTION

This invention pertains to a neuroendocrine protein antigen which is associated with Type I diabetes mellitus, to nucleic acid encoding the protein and to methods and reagents for detecting antibody against the protein and identifying individuals at risk of developing Type I diabetes mellitus. The protein, designated PM-l, is a 69 kD antigen (determined by sodium dodecyl sulfate-polyacrylamide gel electrophoresis (SDS-PAGE)) expressed by human pancreatic islet cells. The nucleotide sequence of cDNA encoding the PM-1 protein and the deduced amino acid sequence of the protein have been determined and are shown in the Sequence Listing. PM-1 protein can be produced by isolating the protein from cells which express the protein, such as islet cells, or cells derived therefrom, or by synthesizing the protein chemically or by recombinant DNA techniques.

Autoantibodies to the PM-1 protein have been found in serum of some prediabetic individuals (who later developed overt diabetes) but have not been found in serum of non-diabetic individuals. Thus, anti-PM-1 autoantibodies are associated with development of diabetes. Immunoreactive forms of the PM-1 protein can be used in immunochemical assays to detect the presence of such autoantibodies in biological fluid to thereby identify individuals at risk of developing diabetes. The PM-1 protein, or an antigenic fragment thereof, are useful in methods to treat or prevent the development of Type I diabetes. Therapeutic compositions containing the PM-1 protein or an antigenic fragment can be administered to a diabetic individual or a prediabetic individual at risk of developing diabetes, to tolerize the individual or block the immune response of the individual to the PM-1 protein.

BRIEF DESCRIPTION OF THE DRAWINGS

FIG. 2 is the nucleotide sequence and deduced amino acid sequence of the PM-1 protein. Underlined are: (a) the first upstream in frame stop codon (TAA) at nucleotide −72; and (b) polyadenylation signal 23 bp upstream of the poly(A) tail. Homologous subunits with bovine serum albumin (BSA) are in boxes. The potential N-linked glycosylation site is indicated by asterisk. Potential phosphorylation sites are as follows: PKC (protein kinase C); CK2 (casein kinase II) and AMP (cAMP/cGMP-dependent kinase). The amidation site is indicated as AMD.

FIG. 4 shows regions of similarity between the PM-1 protein and BSA.

DETAILED DESCRIPTION OF THE INVENTION

Figure 1:
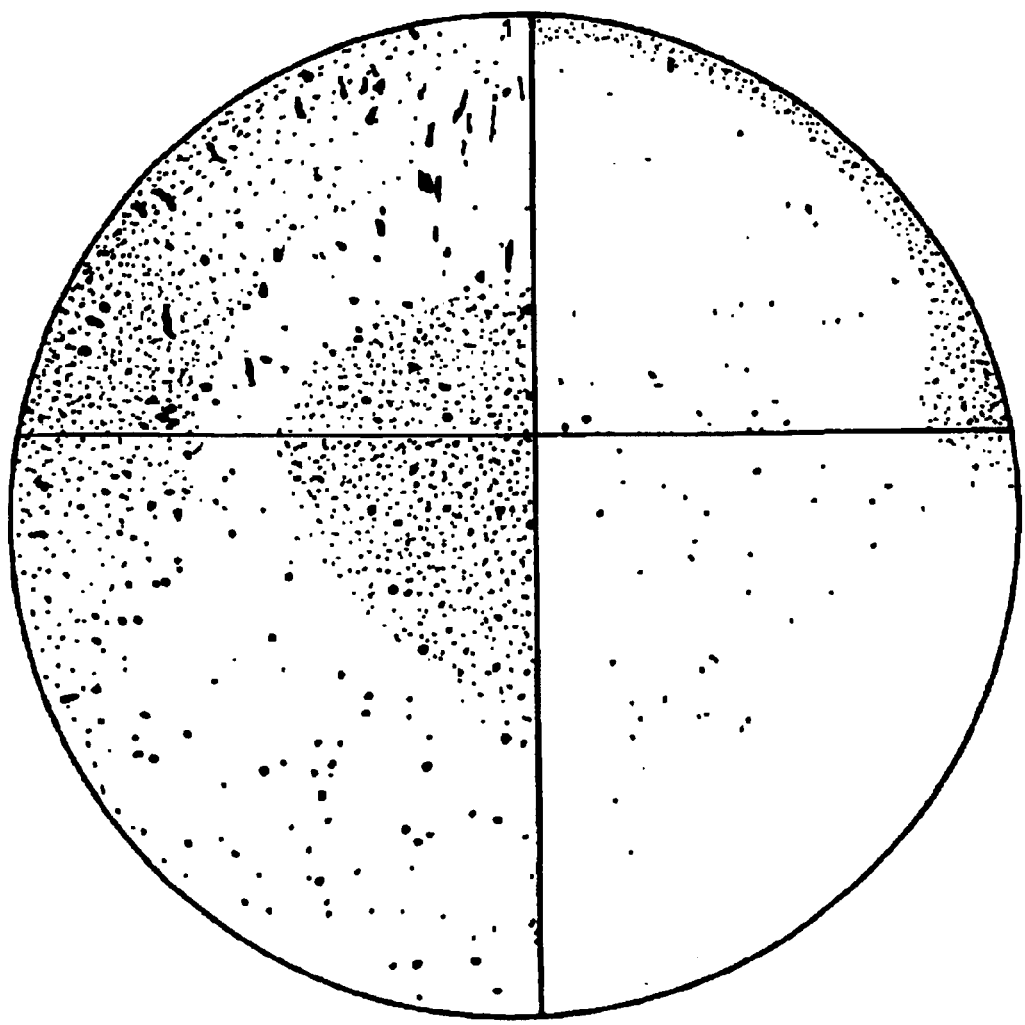
FIG. 1 shows the reactivity of sera from a prediabetic patient with purified PM-1 clone. The clone did not react with a control sera.
Figure 3:
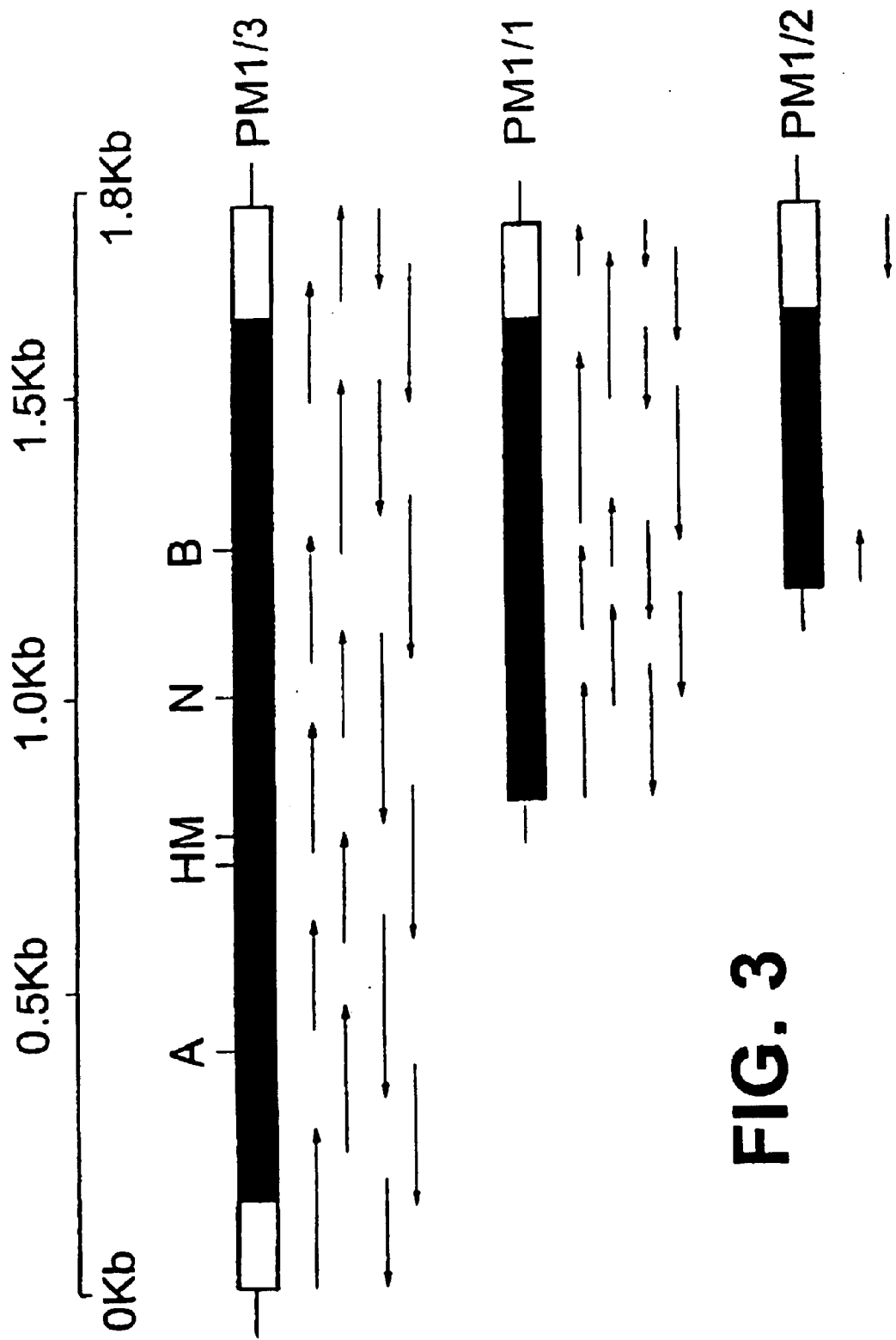
FIG. 3 is a schematic representation of the strategy used to sequence cDNA encoding the PM-1 protein. The direction of sequencing using synthetic oligonucleotide primers is indicated by arrows. Restriction sites are A:Acc II, B:Bgl II, H:Hgi AI, M:Mae II, and N:Nde I.

The PM-1 protein, is a neuroendocrine protein having a molecular weight of about 69 kD (determined by SDS-PAGE). The PM-1 protein is expressed by human pancreatic β-islet cells and a human insulinoma. The amino acid sequence of the PM-1 protein and the nucleotide sequence of cDNA encoding the protein are given in the Sequence Listing below.

The PM-1 cDNA comprises a 1785 bp nucleotide sequence which includes a 5' 178-noncoding sequence of a 1449-bp open reading frame and a 3' 155 bp-noncoding sequence. The open reading frame of the cDNA that can be translated from two mRNA species of 2 Kb and 5 Kb respectively, predicts a 483 amino acid protein, with a potential N-linked glycoslation site. A canonical polyadenylation signal AATAAA is present 23 bp up-stream of the poly(A) tail. The native PM-1 molecule migrates to 69 kD in a SDS-PAGE as detected with specific antibodies generated to an internal and a C-terminus polypeptide.

The PM-1 protein can be obtained in native form by isolation from cells which express the antigen such as cell lines derived from β-islet cells. Alternatively, the protein may be synthesized chemically by, for example, the solid phase process of Merrifield.

The PM-1 protein can also be produced as a recombinant protein. Nucleic acid (DNA or RNA) encoding the PM-1 protein is inserted into an expression vector, such as a plasmid or viral nucleic acid, in conjunction with appropriate genetic regulatory elements. Nucleic acid encoding PM-1 protein can be produced de novo by, for example, the cDNA cloning procedures described below or it can be obtained from available clones. Alternatively, DNA encoding PM-1 protein can be synthesized chemically according to the nucleotide sequence (or a functional equivalent thereof) given in the Sequence Listing. The recombinant vector is then introduced into a vector compatible host cell. The host cell is cultured in a suitable medium, under conditions which allow expression and, if appropriate, secretion of the protein. Isolation of the recombinant PM-1 protein from the cells or cell culture medium can be accomplished by standard procedures, including ion-exchange chromatography, gel filtration chromatography, ultrafiltration, electrophoresis or immunopurification with antibodies specific for the protein. PM-1 protein is isolated such that the protein is substantially free of cellular material or culture medium when produced by recombinant DNA techniques, or substantially free of chemical precursors or other chemicals when synthesized chemically.

Antigenic fragments or peptides derived from the PM-1 protein are within the scope of the invention. Fragments within the scope of the invention include those which induce an immune response in mammals, preferably humans, such as the production of IgG and IgM antibodies or elicit a T-cell response such as T-cell proliferation and/or lymphokine secretion and/or the induction of T-cell anergy. Fragments of the nucleic acid sequence coding for the PM-1 protein are also within the scope of the invention. As used herein, a fragment of a nucleic acid sequence coding for the PM-1 protein refers to a nucleotide sequence having fewer bases than the nucleotide sequence coding for the entire amino acid sequence of the PM-1 protein. Nucleic acid sequences used in any embodiment of this invention can be cDNA as described herein, or alternatively, can be any oligodeoxynucleotide sequence having all or a portion of a sequence represented herein, or their functional equivalents. Such oligodeoxynucleotide sequences can be produced chemically or mechanically using known techniques. A functional equivalent of an oligonucleotide sequence is one which is capable of hybridizing to a complementary oligonucleotide to which the sequence shown in the Sequence Listing or fragment thereof hybridizes or a sequence complementary to the sequence shown in the Sequence Listing.

Given the nucleic acid sequence and deduced amino acid sequence of the PM-1 protein, it is possible to identify peptides which contain T- or B-cell epitopes. An epitope is the basic element or smallest unit of recognition by a receptor where the epitope comprises amino acid residues essential to receptor recognition. For example, peptides containing T cell epitopes associated with interaction with the T-cell receptor (TCR) on helper T-cells can be identified. These T cell epitopes are usually at least 7 amino acid residues in length and, when associated with the MHC II glycoprotein present on the surface of antigen-presenting cells, form a complex that interacts with the TCR. Relevant peptides comprising at least one T cell epitope of the PM-1 protein can be identified by dividing the PM-1 protein into overlapping or non-overlapping peptides of desired lengths, which may be produced recombinantly or synthetically. The peptides can be cultured in the presence of antigen-presenting cells in a standard T-cell proliferation assay to determine the ability of the peptide to stimulate T-cell proliferation as indicated by, for example, cellular uptake of labeled thymidine. Peptides derived from the PM-1 protein with altered structures can be designed which retain their ability to complex with MHC II glycoprotein but fail to effect reaction with TCR by assessing the ability of these altered peptides to inhibit the T-cell proliferation in the presence of known activators in this assay.

It is possible to modify the structure of the PM-1 protein or peptide thereof for such purposes as increasing solubility, enhancing therapeutic or preventive efficacy, or stability (e.g., shelf life ex vivo, and resistance to proteolytic degradation in vivo). A modified PM-1 protein or modified peptide can be produced in which the amino acid sequence has been altered, such as by amino acid substitution, deletion, or addition, to modify immunogenicity and/or increase therapeutic effectiveness or to which a component has been added for the same purpose. For example, additional amino acid residues derived from the PM-1 sequence or other sequence can be attached to either the amino terminus, the carboxy terminus, or both the amino terminus and carboxy terminus of the PM-1 protein. Non-PM-l derived sequences include residues which may increase solubility or facilitate purification, such as a sequence attached to the PM-1 protein to aid purificiation of protein produced by recombinant technique. Site-directed mutagenesis of DNA encoding the PM-1 protein or a peptide thereof can be used to modify the structure of the PM-1 protein or peptide. Such methods may involve PCR (Ho et al., *Gene*, 77:51–59 (1989)) or total synthesis of mutated genes (Hostomsky, Z., et al. *Biochem Biophys. Res. Comm.*, 161:1056–1063(1989)).

The PM-1 protein can be employed in novel therapeutic methods to treat an autoimmune disease in an individual. The PM-1 protein, or antigenic fragment thereof, can be administered to a diabetic or prediabetic individual to prevent the progression or development of Type I diabetes in the individual. The PM-1 protein, or at least one antigenic fragment, in the form of a therapeutic composition, is administered simultaneously or sequentially to the individual in an amount effective to prevent the progression or development of diabetes in the individual. In addition, the therapeutic composition can be administered under non-immunogenic conditions to tolerize the individual to the PM-1 protein, rather than elicit an immune response. As used herein, tolerization is defined as non-responsiveness or diminution in symptoms upon exposure to the PM-1 protein. Techniques for administration of tolerizing doses of antigens are known in the art, including administration of the PM-1 protein, or fragment thereof, in the absence of adjuvant and/or in soluble form. Administration of a peptide derived from the PM-1 protein comprising at least one T cell epitope may tolerize appropriate T cell subpopulations such that they become unresponsive to the PM-1 protein. Therapeutic methods that utilize antagonist peptides of the PM-1 protein which bind the MHC II glycoprotein but result in a complex which is not interactive with the TCR can also be used.

The PM-1 protein or peptide thereof may be administered alone or in concert with anti-CD4 antibodies or other CD4 blockers. This approach to conferring tolerance is disclosed in U.S. Pat. Nos. 4,681,760 and 4,904,481. In this approach, the antigen and the anti-CD4 antibodies or immunoreactive fragments are administered concomitantly. By "concomitant" administration is meant within a time frame which permits the anti-CD4 component to block the helper T-cell response to the antigen. The nature of "concomitant" in this sense is described in the above-referenced U.S. patents, incorporated herein by reference.

The PM-1 protein or fragment thereof is combined with a pharmaceutically acceptable carrier or diluent to form a therapeutic composition. Pharmaceutically acceptable carriers include polyethylene glycol (Wie et al. *International Archives of Allergy and Applied Immunology* 64:84–99 (1981)) and liposomes (Strejan et al. *Journal of Neuroimmunology* 7:27 (1984)). Pharmaceutically acceptable diluents include saline and aqueous buffer solutions. Such compositions will generally be administered by injection subcutaneously, intravenously or intraperitoneally, oral administration, (e.g., as in the form of a capsule) inhalation, transdermal application or rectal administration.

Sequence analysis of the PM-1 protein revealed two regions of similarity with bovine serum albumin (BSA) (FIG. 4). These regions of similarity may contain epitopes shared by the PM-1 molecule and BSA. It has been shown that many patients with Type I diabetes have elevated levels of anti-IgG anti-BSA antibodies. Thus, BSA may represent a target antigen for cow milk induced islet autoimmunity (Martin, J. M., et al., supra). Peptides comprising amino acid residues shared by the PM-1 protein and BSA may be useful in the form of a therapeutic composition to treat an autoimmune disease, such as Type I diabetes in an individual. A therapeutic composition comprising a pharmaceutically acceptable carrier or diluent and one or both of the following peptides can be administered: Phe-Asp-Lys-Leu-Lys-$Xaa_1$-$Xaa_2$-Val; and $Xaa_3$-$Xaa_4$-Gly-Ala-Cys-Leu-$Xaa_5$-Pro, where $Xaa_1$ is Met or His, $Xaa_2$ is Asp or Leu, $Xaa_3$ is Glu or Asp, $Xaa_4$ is Glu or Lys, and $Xaa_5$ is Glu or Leu. Such compositions are administered to the individual in an amount effective to treat the autoimmune disease. Additional amino acid residues derived from the PM-1 protein or BSA can be attached to either the amino terminus, carboxy terminus or both the amino terminus and carboxy terminus of these peptides.

Antibodies reactive with the PM-1 protein can be produced by standard techniques. An animal such as a mouse or rabbit is immunized with-an immunogenic form of the PM-1 protein (e.g., all or a portion of the PM-1 protein which is capable of eliciting an antibody response). Techniques for conferring immunogenicity on a protein or peptide subunit include conjugation to carriers or other techniques well known in the art. The PM-1 protein or immunogenic peptide can be administered in the presence of adjuvant. The progress of immunization can be monitored by detection of antibody titers in plasma or serum standard ELISA or other immunoassay can be used with the immunogen as antigen to assess the levels of antibodies.

Following immunization, anti-PM-1 antisera is obtained and, if desired, polyclonal anti-PM-1 antibodies isolated from the serum. To produce monoclonal antibodies, antibody producing cells (lymphocytes) are harvested from an immunized animal and fused by standard somatic cell fusion procedures with immortalizing cells such as myeloma cells to yield hybridoma cells. Hybridoma cells can be screened immunochemically for production of antibodies reactive with the PM-1 protein.

Autoantibodies to the PM-1 protein have been found in serum of some ICA positive prediabetic individuals (who later developed overt diabetes). These autoantibodies have not been found in the serum of non-diabetic individuals. Anti-PM-1 autoantibodies are associated with development of diabetes and the detection of these antibodies in an individual provides an indication of the individual's risk of developing diabetes.

The PM-1 protein can be used in immunochemical assays to detect the presence of autoantibodies against the antigen in a biological fluid and identify an individual at risk of developing diabetes. The PM-1 protein is contacted with the biological fluid to be tested under conditions which allow the antigen to complex with antibody in the fluid. The detection of complexes formed between the PM-1 protein or peptide and antibody is indicative of the presence of antibody against PM-1 protein in the fluid.

A preferred assay type is a solid phase immunometric assay. In assays of this type, purified PM-1 protein is immobilized on a solid phase support. The support is incubated with the sample of biological fluid to be tested. The incubation is performed under conditions which allow complexation between immobilized PM-1 protein and antibody against the protein. The solid phase support is then separated from the sample and a labeled anti-(human IgG) antibody is used to detect human anti-PM-1 antibody bound to the support. The amount of label associated with the support is compared to positive and negative controls to assess the presence or absence of anti-PM-1 antibody.

In these assays, an immunoreactive form of the PM-1 protein or peptide thereof are used. Native, synthetic or recombinant purified forms of the whole molecule, or portions immunoreactive with an antibody against PM-1 may be used. In addition, modified PM-1 protein which has an amino acid sequence sufficiently duplicative of the PM-1 amino acid sequence (given in the Sequence Listing) so that they are immunoreactive with an autoantibody against PM-1 and provide an assay of suitable sensitivity and reliability can be used.

In the solid phase immunometric assay, purified PM-1 antigen can be adsorbed or chemically coupled to a solid phase support. Various solid phase supports can be used, such as beads formed of glass, polystyrene, polypropylene, dextran or other material. Other suitable solid phase supports include tubes or plates formed from or coated with these materials.

The PM-1 protein can be either covalently or non-covalently bound to the solid phase support by techniques such as covalent bonding via an amide or ester linkage or adsorption. After the PM-1 protein is affixed to the solid phase, the solid phase support can be post-coated with an animal protein to reduce non-specific adsorption of protein to the support surface.

The support containing PM-1 protein functions to selectively insolubilize antibody in the liquid sample tested. In a blood test for anti-PM-1 antibody, the support is incubated with blood plasma or serum. Before incubation, plasma or serum can be diluted with normal animal plasma or serum. The diluent plasma or serum is derived from the same animal species that is the source of the anti-(human IgG) antibody. The preferred anti-(human IgG) antibody is goat anti-(human IgG) antibody. Thus, in the preferred format, the diluent would be goat serum or plasma.

The conditions of incubation, e.g., pH and temperature, and the duration of incubation are not crucial. These parameters can be optimized by routine experimentation. Generally, the incubation will be run for 1–2 hours at about 45° C. in a buffer of pH 7–8.

After incubation, the solid phase support and the sample are separated by any conventional technique such as sedimentation or centrifugation. The solid phase support then may be washed free of sample to eliminate any interfering substances.

To assess human antibody bound to the solid phase support, a labeled anti-(human IgG) antibody (tracer) is used. Generally, the solid phase support is incubated with absolution of the labeled anti-(human IgG) antibody which contains a small amount (about 1%) of the serum or plasma of the animal species which serves as the source of the anti-(human IgG) antibody. Anti-(human IgG) antibody can be obtained from any animal source. However, goat anti-(human IgG) antibody is preferred. The anti-(human IgG) antibody can be an antibody against the $F_C$ fragment of human IgG, for example, goat anti-(human IgG) $F_C$ antibody.

The anti-(human IgG) antibody can be labeled with a radioactive material such as $^{125}$Iodine, with an optical label, such as a fluorescent material, or with an enzyme such as horseradish peroxidase. The antihuman antibody can also be biotinylated and labeled avidin used to detect its binding to the solid phase support.

After incubation with the labeled antibody, the solid phase support is separated from the solution and the amount of label associated with the support is evaluated. The label may be detected by a gamma counter if the label is a radioactive gamma emitter, or by a fluorimeter, if the label is a fluorescent material. In the case of an enzyme, the label may be detected colorimetrically employing a substrate for the enzyme.

The amount of label associated with the support is compared with positive and negative controls in order to determine the presence of anti-PM-1 antibody. The controls are generally run concomitantly with the sample to be tested. A positive control is a serum containing antibody against the PM-1 protein; a negative control is a serum from individuals (e.g., non-prediabetic individuals) which does not contain antibody against the PM-1 protein.

For convenience and standardization, reagents for the performance of the solid phase assay can be assembled in assay kits. A kit for screening blood, for example, can include the following components in separate containers:

(a) a solid phase support coated with PM-1 protein;

(b) optionally, a diluent for the serum or plasma sample, e.g., normal goat serum or plasma;

(c) a labeled anti-(human IgG) antibody, e.g., goat anti-(human IgG) antibody in buffered, aqueous solution containing about 1% goat serum or plasma;

(d) optionally, a positive control, i.e., serum containing antibody against PM-1 protein; and (e) optionally, but preferred, a negative control, e.g., serum which does not contain antibody against PM-1 protein.

If the label is an enzyme, an additional component of the kit can be the substrate for the enzyme.

Other assay formats can be used to test for antibody against the PM-1 protein. One type is an antigen sandwich assay. In this assay, a labeled PM-1 protein is used in place of anti-(human IgG) antibody to detect anti-PM-1 antibody bound to the solid phase support. The assay is based in principle on the bivalency of antibody molecules. One binding site of the antibody binds the antigen affixed to the solid phase support; the second is available for binding the labeled antigen. The assay procedure is essentially the same as described for the immunometric assay except that after incubation with the sample, the support is incubated with a solution of labeled PM-1 protein. The PM-1 protein can be labeled with radioisotope, an enzyme, etc. for this type of assay.

The following examples describe the isolation of cDNA clones from a human islet λgtll expression library using sera of prediabetic patients. The putative polypeptide encoded by the longest open reading frame of PM-1 clones has a molecular weight of 54,600. On Western blots immunoreactive PM-1 has a molecular weight of 69 kD suggesting glycosylation or aberrant migration on SDS-PAGE.

EXAMPLE 1

Isolation of Clones Encoding PM-1 cDNA From λgtll Expression Libraries

Two libraries, a human islet library and a human insulinoma library were used to identify and isolate clones encoding PM-1 cDNA. A λgtll cDNA library was constructed from human islet poly(A+) RNA by Clontech (Palo Alto, Calif.). Approximately 1×10$^6$ plaques were obtained with 80% being recombinants. Human Insulinoma poly(A+) RNA was isolated and then cDNA produced and packaged into the λgtll phage (Huynh, J. V., et al. (1985) In: Glover DM (ed) DNA Cloning Techniques. IRL Press, Oxford pp. 49–78).

Sera obtained from first degree relatives of patients with Type I diabetes which patients had progressed to overt disease and who expressed high titers of Islet Cell Antibodies (>80 Juvenile Diabetes Foundation Units) were used to screen the libraries. The sera were repeatedly absorbed with a protein lysate of a wild type λgtll-infected *Escherichia coli* (Y1090) (Sambrook, J., et al. (1989) Molecular Cloning: A Laboratory Manual, 12-25-12.28, Cold Spring Harbor Laboratory Press, Cold Spring Harbor, N.Y.) in order to remove anti-*E. coli* antibodies. The absorbed sera, either controls or relatives' sera, that continued to give an unacceptably high level of reactivity to host cells were not utilized. The absorbed antibodies were stored at −20° C. in the presence of 0.05% sodium azide until used for immunological screening. Originally, a pool of three sera were used to identify a positive clone and subsequently sera of three other relatives were studied. Ten normal individuals' sera were also tested for reactivity with the positive clone.

The phage human islet λgt11 expression library was screened with the sera from prediabetic relatives obtained as described above (Young, R. A. and R. W. Davis (1984) Science 222: 778–782). Isolated recombinant phages were plated on a Luria-Bertani agar plate (150 mm diameter) with Escherichia coli strain (Y1090) at approximately 1×10⁴ plaque-forming units per plate. After a 3 hour incubation at 42° C., a nitrocellulose filter (Schleicher & Schuell) saturated with 10 mM isopropyl β-D-thiogalactopyranoside (IPTG; BRL) was overlaid on the agar overnight at 37° C. to induce the expression of β-galactosidase fusion proteins. Following blocking with 1% bovine serum albumin (Sigma) in 1×Tris-Buffer Saline 0.05% Tween (incubation for two hours at room temperature), the plates were incubated with 1/500 diluted sera overnight at 4° C. After several washes with 1×Tris Buffer Saline 0.05% Tween, the bound antibodies were detected by incubation with anti-human IgG alkaline phosphatase 1/100 diluted (two hours at room temperature) (Cappel, Durham, N.C.).

The phage λgt11 library was initially screened with the pool of sera from three prediabetics. The original positive plaque was replated and rescreened by repeating sequentially until all progeny of plaques were recognized by the sera. Individual sera were then incubated with a mixture of the positive clone and several negative clones, in order to reduce the possibilities of false positivity and to score reactivity of individual sera.

From the human islet λgt11 expression library, approximately 0.4×10⁶ plaques were screened and the PM-1 molecule was identified. This clone was recognized by 3 out of 6 ICA positive prediabetic subjects' sera (at a dilution of 1:500 of the sera) when its fusion protein was induced by isopropyl thiogalactoside (IPTG), whereas the clone did not react with 10 control individual sera (FIG. 1). The clone designated PM-1 was 0.95 Kb. A labeled cDNA probe derived from the PM-1 clone was used to screen both a human λgt11 islet library and a human insulinoma λgt11 library by plaque hybridization, in order to obtain the full length of the molecule (Feinberg, A. P. and B. Vogelstein (1983) Anal. Biochem. 132:6–13). Two additional hybridizing and overlapping clones were identified from the human islet λgt11 expression library after screening approximately 3.5×10⁴ plaques. The largest clone contained a 1.78-Kb insert with an internal EcoRI site. The probe was labeled with (alpha $^{32}$P) dCTP by random priming (Wallace, R. B., et al. (1981) Nucleic Acids Res, 9:879–894) using Klenow fragment (Amersham Corp.) and used to rescreen the libraries. DNA sequence analysis (see below) confirmed that the clones contained fragments of the same gene.

EXAMPLE 2

Amplification of λgt11 cDNA Insert and Cloning of the PM-1 Protein

The λgt11 cDNA insert from the positive clone was amplified by Polymerase Chain Reaction (PCR) (Friedman, K. D., et al. (1988) Nucleic Acids Res, 16:8718; and Innis, M., et al. In: A Guide to Methods and Applications. Academic Press, New York (1990)), using λgt11 primers complementary to the β-galactosidase portion of the λgt11 template (Primer n. 1218: 5' GGTGGCGACGACTCCTGGAGC-CCG 3'; and Primer n. 1222: 5' TTGACACCAGAC-CAACTGGTAATG 3', New England Biolabs). Reaction mixtures for PCR (0.1 ml) contained cDNA template, 100 pmol each of the primers and 2.5 units of Taq DNA Polymerase (Perkin-Elmer/Cetus) in 10 mM Tris.HCl, pH 8.3, 50 mM KCl, 1.5 mM MgCl$_2$ containing dNTPs at 0.2 mM each and 0.01% gelatin. Reactions were carried out in a Perkin-Elmer/Cetus thermal cycler for 30 cycles of denaturation (92° C., 1.5 minutes), annealing (55° C., 1.5 minutes), and elongation (72° C., 1 minute). After EcoRI digestion and fractionation on 1% agarose gel stained with ethidium bromide to visualize the products, the PCR product of interest was excised, purified and subcloned into the EcoRI site of pBluescript II vector (Stratagene, La Jolla, Calif.). DNA samples for PCR were obtained from phage suspension.

Nucleotide sequences were determined by using the dideoxynucleotide chain termination method of Sanger et al. (Sanger, F. et al. (1977) Proc. Natl. Acad. Sci. USA 74:5463–5467), employing T7 DNA polymerase (Sequenase: United States Biochemical, Cleveland, Ohio). To avoid compression in G+C-rich sequences, some sequencing reactions were performed with dITP alternating with dGTP (Tabor, S. and C. C. Richardson Proc. Natl. Acad. Sci. USA 84:4767–4771).

Following PCR amplification and pBluescript subcloning, partial sequence indicated that the smallest-overlapping clone, whose size is 0.6 kD, reveals a sequence totally contained within the original sequenced PM-1 insert (FIG. 2). The results of sequencing both cDNA strands of the largest clone, whose size is 1.78 Kb, indicates complete identity in the region of the molecule overlapping with PM-1 and the second clone, and sequence not contained within the previous clone. Analysis of the nucleotide sequence reveals 1785 bases in length with a 1449 base open reading frame coding for 483 amino acids and ending in a poly(A) tail 23 bases downstream of the polyadenylation signal (AATAAA). Translation of the PM-1 molecule putatively initiates from the first in frame ATG according to the criteria defined by Kozak (Kozak, M. (1987) Nucl. Acid Res. 15(20) :8125–8132). Upstream from the first ATG, there is an in frame stop codon (TAA) at −72 bp. The predicted open reading frame from the deduced ATG start codon codes for a protein with an estimated linear $M_r$ of 54, 600, which contains one potential N-linked glycosylation site (FIG. 2).

Sequences were aligned and analyzed using the EUGENE, SAM, PIMA.SH and PROSITE programs. The GenBank (DNA and Amino Acid databank) was searched for homologies and the PLSEARCH program was analyzed for protein sequence patterns derived from the sequences of homologous protein families (Molecular Biology Computing Research Resource, Dana Farber Cancer Institute and Harvard School of Public Health). No significant amino acid or nucleic acid similarities were found, with the exception of bovine serum albumin (BSA). Two regions of BSA appear to have similarities with the PM-1 protein, suggesting that the PM-1 protein may share potential immunogenic epitopes with BSA (FIG. 4). It is known that antibodies to bovine serum albumin cross-react with an islet protein of $M_r$ 69,000, which can be induced by interferon in RIN tumor cell lines (Martin, J. M., et al. (1991) Ann. Med. 23:447–452; and Dosh, H. M., et al. (1991) Pediatr. Adolesc. Endocrinol. 21). It has been reported that antibodies raised to one short BSA unique peptide region (amino acid residues 154–169) on a Western Blot format react with RIN as well as islet proteins with a similar mobility (60–70 kD) than serum from newly diagnosed IDDM patients. The identity of these islets and RIN tumor BSA cross-reacting protein(s) has not yet been clarified.

Figure 5:
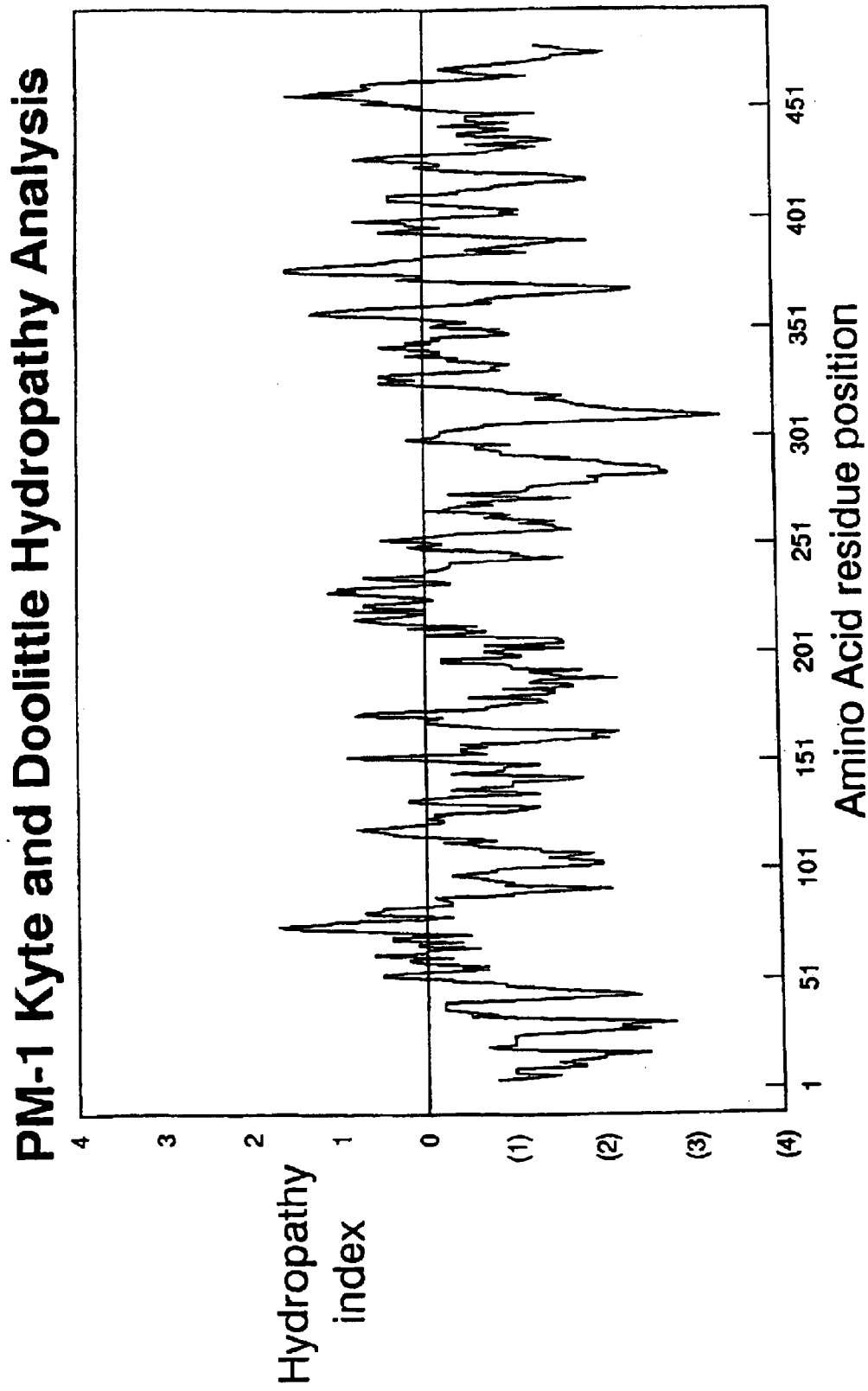
FIG. 5 is a Kyte & Doolittle hydrophobicity plot generated using the deduced amino acid sequence of the PM-1 protein.

A hydrophobicity plot (FIG. 5) generated from the PM-1 deduced amino acid sequence reveals a number of slightly hydrophobic regions, alternated by several very hydrophilic segments, which suggests that the molecule does not contain any membrane spanning domains, according to the criteria defined by Kyte and Doolittle (*J. Mol. Biol.* (1985) 157:105–132) and Klein, et al. (*Biochem. Biophys. Acta* (1985) 815:468–476). The segments of hydrophobicity do not appear not to be long enough to be potential transmembrane-spanning regions. The molecule is extremely hydrophilic with approximately ⅓ of its amino acid residues charged.

EXAMPLE 3

Production of Anti-PM-1 Antibodies from Synthetic Peptides Derived From PM-1

Peptides were synthesized from the deduced amino acid sequence of PM-1 and used to immunize rabbits to generate antibodies against specific domains (Van Regenmortel, M. H. V., et al. (1988) In: Laboratory Techniques in Biochemistry and Molecular Biology (R. H. Burden and P. H. von Knippenberg, eds.) Elsevier, New York and Amsterdam). Two regions of the molecule, one corresponding to the C-terminus, residues 471–483: GKTDKEHELLNA, and one to an internal polypeptide near the C-terminus residues 458–470: ADLDPLSNPDAV were utilized and found to yield antisera which immunoprecipitate the native PM-1 molecule. The synthetic polypeptides were coupled to a carrier protein Keyhole Limpet Hemocyanin (KLH) linked to bromoacetyl bromide. Four female New Zealand white rabbits were immunized with 1 mg of the KLH-peptide conjugate suspended in 1 ml of complete Freund's adjuvant. The rabbits were boosted twice with a further 1 mg of the specific polypeptide in incomplete Freund's adjuvant at 30 day intervals and serum samples were collected and stored in aliquots at −20° C.

An indirect ELISA assay was performed in order to detect specific antibodies against the PM-1 polypeptides (Harlow, E. and D. Lane (1988), Antibodies: A Laboratory Manual. Cold Spring Harbor Laboratory, Cold Spring Harbor, N.Y.). 1 μg of specific polypeptide was used to coat each well of an Immulon microtiter plate, and after blocking residual binding of plate with a 1% BSA PBS solution for two hours, appropriate dilutions of rabbit pre- and post-immune sera were added to each well (1:100–1:32,000) and incubated overnight. All the points were done in triplicate. After washing away unbound antibodies, a solution containing Anti-Rabbit IgG (whole molecule) Peroxidase Conjugate (Sigma) as developing reagent was added to the wells. After two hours incubation, unbound conjugate was washed away and a substrate solution (o-Phenylenediamine Dihydrochloride, OPD, Sigma), was added. The O.D. of the solutions in the wells was assessed with a spectrophotometer.

EXAMPLE 4

Northern Analysis of RNA From Various Cell Lines and Tissues with PM-1 Probes The cDNA derived from several PM-1 clones was used to probe for transcripts in human and animal tissues and in several cell lines by Northern blotting. Total RNAs and poly(A+) RNAs from various tissues and cell lines were prepared by the guanidinium method, enriched for the polyadenylated (poly-A) fraction with oligo(dT)-cellulose column and analyzed on Northern blots according to standard procedures (Thomas, P. S. (1980) *Proc. Natl. Acad. Sci. USA*). The hybridization was carried out for 18 hours at 42° C. in the prehybridization buffer (50% formamide, 5×SSPE (1×SSPE consists of 150 mM NaCl, 10 mM sodium phosphate and 1 mM EDTA, pH 7.4, 5× Denhardt's solution, 100 μg/ml denaturated salmon sperm DNA, and 0.1% SDS) (Sambrook, J. et al. (1989) Molecular Cloning: A Laboratory Manual, 12-25-12.28, Cold Spring Harbor Laboratory Press, Cold Spring Harbor, N.Y.) containing alpha $^{32}$P dCTP labeled cDNA purified probe. The probes used were 0.95 Kb derived from the original PM-1 positive clone identified and 1.78 Kb from an overlapping clone. The nitrocellulose filters were washed in three changes of 2×-SSC and 0.1% SDS at room temperature each time. The final two washes were carried out in 0.25 SSC and 0.1% SDS from room temperature to 65° depending upon the stringency conditions required for each experiment. Filters were exposed to Kodak film at −70° C. with intensifying screens. Ribosomal bands were used as size markers (Hassoina, N., et al. (1984) *Nucl. Acids Res,* 12:3563; and Raynal, F., et al. (1984) *FEBS Lett.* 167:263).

Figure 6:
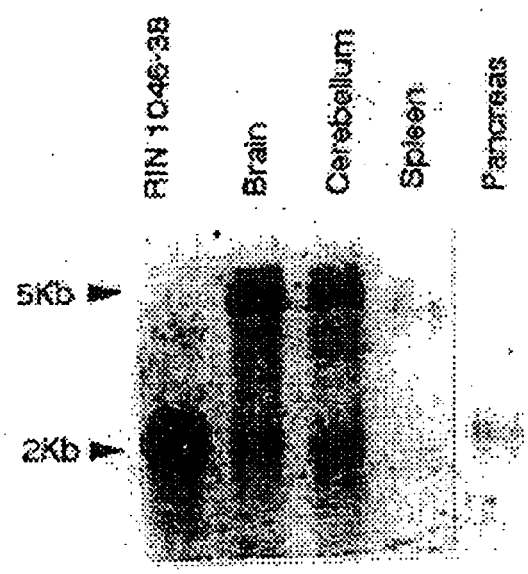
FIG. 6 shows the results of Northern blot analysis of total mRNA from a cell line and various tissues with a PM-1 cDNA probe. The probe hybridized with a 2 Kb mRNA in total RNA from rat pancreas, brain, cerebellum (in the latter two tissues with an additional 5 Kb band). Hybridization with a 2 Kb total RNA band was also detected with a rodent islet cell (RIN 1046-38).
Figure 7:
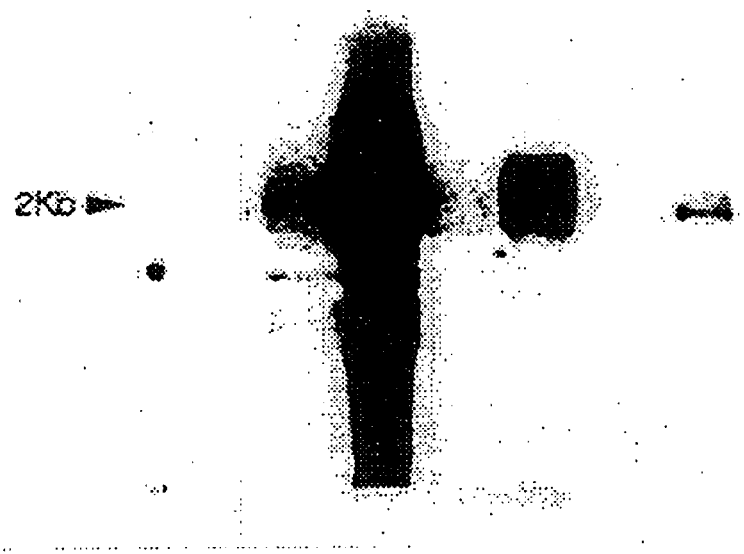
FIG. 7 shows the results of Northern blot analysis of total RNA from various cell lines with a PM-1 cDNA probe. The probe hybridized with RNA from a human islet carcinoid cell line (BON-1) and three rodent islet cell lines (RIN 1046-38, beta TC-1 and alpha TC-6) but not with RNA from non-islet cell lines (HepG2-hepatoma, HeLa-fibroblast, JEG-choriocarcinoma).

Both the 0.95 Kb and 1.78 Kb cDNA probes hybridized with an mRNA band of 2 Kb from islet derived cells, and in some tissues, with a 5 Kb band. The labeled cDNA PM-1 insert hybridizes with a 2 Kb mRNA in total RNA from rat pancreas, brain, cerebellum (in the latter two tissues also with a 5 Kb band) (FIG. 6), and lung and kidney (5 Kb band), whereas total mRNA was undetectable in rat heart, thymus, liver, bowel, lymph node and salivary gland. A single 2.0 Kb poly(A+) mRNA was detected in human thyroid and lung, but not in ovary, placenta and spleen. The heterogeneity of mRNA size among tissues may be due to an alternative splicing of the PM-1 gene. Hybridization with a 2 Kb total RNA band was detected in human insulinoma, a human islet carcinoid cell line (BON-1), a hamster insulin-producing cell line (HIT), and 3 rodent islet cell lines, namely RIN 1046-38, β TC-1 (which is visible after longer exposure), α TC-6. No hybridization was detected in total RNA from three human non-islet cell lines, namely HepG2-hepatoma, HeLa-fibroblast, JEG-choriocarcinoma (FIG. 7).

The Northern Analysis of PM-1 transcripts in normal tissues and cell lines evaluated suggest that the PM-1 protein may be related to the neuroendocrine system. The detection of MRNA predominantly in neural tissues, the presence of PM-1 transcripts in islet derived cell lines namely, RIN, BON-1, HIT, β TC-1, α TC-6 and in insulinoma tissue in contrast to non-neuroendocrine cell lines such as HeLa fibroblasts, JEG-choriocarcinoma and HepG2-hepatoma likely reflects the sharing of many molecules between islets and neurons. The low level of PM-1 mRNA in human lung and thyroid and the higher level in kidney could be due to PM-1 transcript expression in the small subpopulation of cells of neuroectodermal origin. Islets and neuronal cells share a large family of molecules of secretory granules like large dense core granules (e.g., containing insulin or carboxypeptidase H) as well as synaptic microvescicular structures (e.g., intracytoplasmic localization of glutamic acid decarboxylase and synatophysin). Many of the molecules of both of these shared structures appear to be prominent targets of the autoimmunity related to Type I diabetes.

EXAMPLE 5

Western Blots of Cells Line Extracts and Tissues With Rabbit Antiserum Directed to the PM-1 Molecule Cell line extracts and total homogenates of rat brain tissues were prepared as described by Laemmli (Laemmli, V. K. (1970) *Nature* (London) 227:680–685). Cell line extracts and total-homogenate proteins were separated by sodium dodecyl sulfate-polyacrylamide gel electrophoresis (SDS-PAGE) and transferred from gel onto nitrocellulose using a constant voltage of 180 V for four hours. The nitrocellulose was cut into strips, and incubated for two hours at 37° C. in 5% nonfat milk diluted in PBS to block the nonspecific binding sites. The nitrocellulose strips were then incubated with a 1:100 dilution of a rabbit antiserum directed against the C-terminus of the PM-1 molecule and then washed in 5% nonfat milk diluted in PBS with 0.01% Tween 20. $^{125}$I-protein A (Amersham), was used to detect bound rabbit anti-PM-1 antibodies. A mixture of individually colored and purified proteins were used as protein standards (RainbowTM Protein Molecular Weight Markers, Amersham): Myosin, MW 200,000, blue; Phosphorylase b, MW 97,400, brown; Bovine serum albumin, MW 69,000, red; Ovalbumin, MW 46,000, yellow; Carbonic anydrase, MW 30,000, orange; Trypsin inhibitor, MW 21,000, green; and Lysozyme, MW 14,300, magenta.

Figure 8:
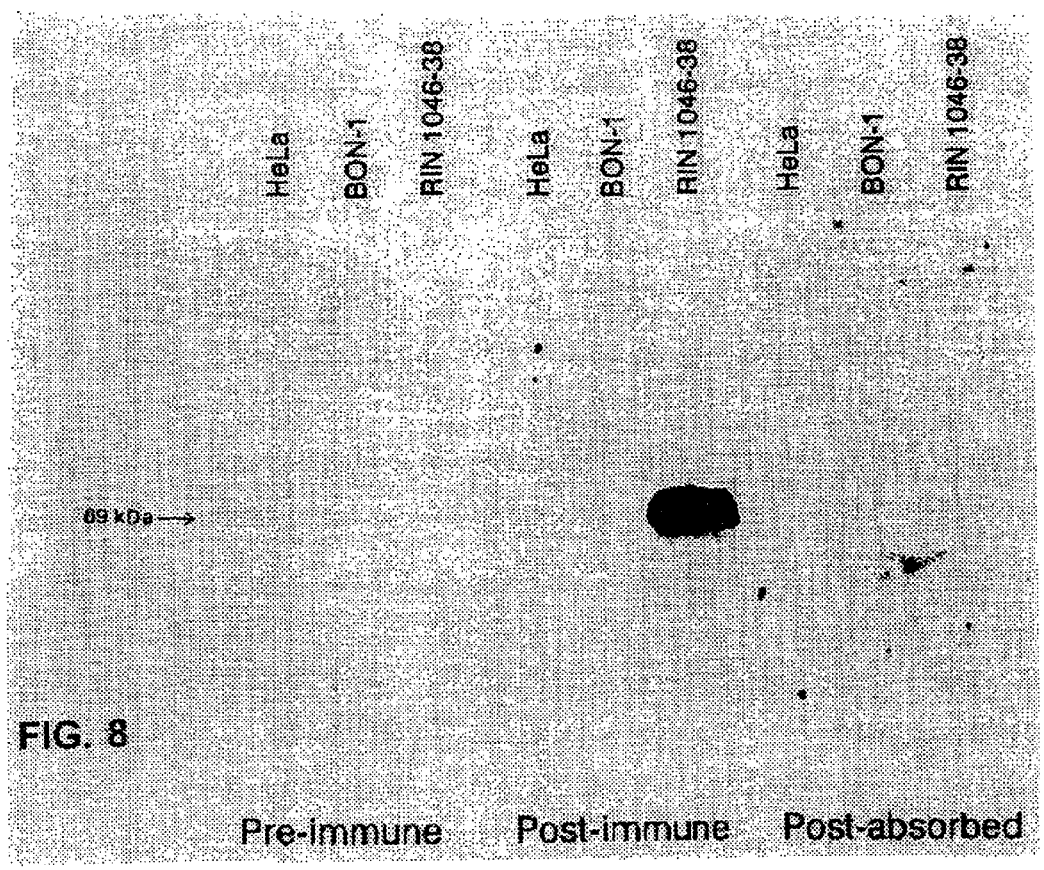
FIG. 8 shows the results of Western Blot analysis of three cell line homogenates. The post-immune antibody generated against the C-terminus of the PM-1 protein appears to recognize a band at 69 kD in RIN 1046-38.

Western blots of brain tissue homogenate and cell line extracts (RIN 1046-38), revealed a specific band of 69 kD following incubation with the rabbit antibodies raised to the C terminus of the PM-1 protein and an internal polypeptide. FIG. 8 illustrates that the anti-C terminus PM-1 serum specifically reacted with a protein of 69 kD in RIN and BON-1 (visible after longer exposure) cell total homogenate but not with HeLa cell line homogenate. In addition, the specific 69 kD band disappears following absorption with the polypeptide for which specific antibodies were yielded. The same specific 69 kD reactivity is also detectable using hyperimmune sera to an internal polypeptide and using rat brain total homogenate. The deduced amino acid sequence of the PM-1 protein is 483 residues with an estimated $M_r$ of 54,600. The difference between the western blot size of the protein fractionated in the SDS-PAGE and the estimated size based upon the deduced amino acid sequence is likely due to a glycosylation of the molecule (Miletich, J. P., et al. (1990) *J. Biol. Chem.* 265:11397–11404; and Bause, E. (1983) *Biochem. J.* 204:331–336). Alternatively, the result of the Western blot may be due to an abnormal migration of the RIN and the brain proteins in SDS-PAGE as a result of solubilzation in detergent-containing buffers as previously observed for other proteins (Kumar, K. N., et al. (1991) *Nature* 354:70–73; and Kumar, K. N., et al. (1991) *J. Biol. Chem.* (266) 23:14947–14952).

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. An isolated nucleic acid comprising the nucleotide sequence shown in SEQ ID NO:1 or a fragment of the nucleotide sequence shown in SEQ ID NO:1 which encodes an antigenic fragment of PM-1 protein.

2. The nucleic acid of claim 1, which is cDNA.

3. The nucleic acid of claim 1 wherein the nucleotide sequence comprises the coding region of the nucleotide sequence shown in SEQ ID NO:1.

4. The nucleic acid of claim 3, wherein the coding region comprises nucleotide 179 to nucleotide 1627 of the nucleotide sequence shown in SEQ ID NO:1.

5. A nucleic acid comprising a nucleotide sequence which is a functional equivalent of the nucleic acid of claim 2.

6. The nucleic acid of claim 5, wherein the nucleotide sequence hybridizes to a nucleotide sequence which is complementary to the nucleotide sequence shown in SEQ ID NO:1.

7. An isolated nucleic acid comprising a nucleotide sequence which encodes the amino acid sequence shown in SEQ ID NO:1 or a nucleotide sequence which encodes an antigenic fragment of the amino acid sequence shown in SEQ ID NO:1.

8. A nucleic acid comprising a nucleotide sequence which is a functional equivalent of the nucleic acid of claim 7.

9. The nucleic acid of claim 8, wherein the nucleotide sequence hybridizes to a nucleotide sequence which is complementary to the nucleotide sequence shown in SEQ ID NO:1.

10. The nucleic acid of claim 7, wherein the antigenic fragment comprises at least one T cell epitope which is recognized by a T cell receptor specific for the PM-1 protein having an amino acid sequence shown in SEQ ID NO:1.

11. The nucleic acid of claim 10, wherein the antigenic fragment comprises at least 7 amino acid residues.

12. The nucleic acid of claim 6, which encodes an amino acid sequence shown in SEQ ID NO:1 which is modified by an amino acid substitution, deletion, or addition.

13. A recombinant expression vector comprising the nucleic acid of claim 7.

14. A recombinant expression vector comprising the nucleic acid of claim 3.

15. A recombinant expression vector comprising the nucleic acid of claim 7.

16. A recombinant expression vector comprising the nucleic acid of claim 10.

17. A host cell transformed with the recombinant expression vector of claim 13.

18. A host cell transformed with the recombinant expression vector of claim 14.

19. A host cell transformed with the recombinant expression vector of claim 15.

20. A host cell transformed with the recombinant expression vector of claim 16.

* * * * *